(12) United States Patent
Shanley et al.

(10) Patent No.: US 7,758,636 B2
(45) Date of Patent: Jul. 20, 2010

(54) EXPANDABLE MEDICAL DEVICE WITH OPENINGS FOR DELIVERY OF MULTIPLE BENEFICIAL AGENTS

(75) Inventors: John F. Shanley, Redwood City, CA (US); Frank Litvack, Los Angeles, CA (US); Theodore L. Parker, Danville, CA (US); Thai Minh Nguyen, Santa Clara, CA (US)

(73) Assignee: Innovational Holdings LLC, New Brunswick, NJ (US)

( * ) Notice: Subject to any disclaimer, the term of this patent is extended or adjusted under 35 U.S.C. 154(b) by 1495 days.

(21) Appl. No.: 11/079,967

(22) Filed: Mar. 14, 2005

(65) Prior Publication Data

US 2006/0122697 A1    Jun. 8, 2006

Related U.S. Application Data

(63) Continuation-in-part of application No. 10/668,430, filed on Sep. 22, 2003.

(60) Provisional application No. 60/412,489, filed on Sep. 20, 2002.

(51) Int. Cl.
*A61F 2/06* (2006.01)
*A61F 11/00* (2006.01)

(52) U.S. Cl. .................. 623/1.42; 623/1.43; 606/108

(58) Field of Classification Search ................ 623/1.15, 623/1.42, 1.43; 606/108, 194, 195
See application file for complete search history.

(56) References Cited

U.S. PATENT DOCUMENTS

| | | | |
|---|---|---|---|
| 5,464,650 | A | 11/1995 | Berg |
| 5,609,629 | A | 3/1997 | Fearnot |
| 5,759,192 | A | 6/1998 | Saunders |
| 5,780,807 | A | 7/1998 | Saunders |
| 5,797,898 | A | 8/1998 | Santini, Jr. |
| 5,824,049 | A | 10/1998 | Ragheb et al. |
| 5,836,964 | A | 11/1998 | Richter et al. |
| 5,873,904 | A | 2/1999 | Ragheb |
| 5,906,759 | A | 5/1999 | Richter |
| 5,972,027 | A | 10/1999 | Johnson |

(Continued)

FOREIGN PATENT DOCUMENTS

DE    20200220    4/2002

(Continued)

OTHER PUBLICATIONS

West, Jennifer L. "Drug Delivery—Pulsed Polymers", Nature Publishing Group, vol. 2, Nov. 2003, pp. 709-710.

(Continued)

*Primary Examiner*—Vy Q Bui

(57) ABSTRACT

An expandable medical device includes a plurality of elongated struts, forming a substantially cylindrical device which is expandable from a cylinder having a first diameter to a cylinder having a second diameter. A plurality of different beneficial agents can be loaded into different openings within the struts for delivery to the tissue. For treatment of conditions such as restenosis, different beneficial agents are loaded into different openings in the device to address different biological processes involved in restenosis and are delivered at different release kinetics matched to the biological process treated. The different beneficial agents may also be used to address different diseases, such as restenosis and acute myocardial infarction from the same drug delivery device.

2 Claims, 5 Drawing Sheets

U.S. PATENT DOCUMENTS

| | | |
|---|---|---|
| 5,972,180 A | 10/1999 | Chujo |
| 5,992,000 A | 11/1999 | Humphrey |
| 5,992,769 A | 11/1999 | Wise |
| 5,994,341 A | 11/1999 | Hunter |
| 5,997,703 A | 12/1999 | Richter |
| 6,066,168 A | 5/2000 | Lau |
| 6,071,305 A | 6/2000 | Brown |
| 6,096,070 A | 8/2000 | Ragheb |
| 6,114,049 A | 9/2000 | Richter |
| 6,123,861 A | 9/2000 | Santini, Jr. |
| 6,131,266 A | 10/2000 | Saunders |
| 6,153,252 A | 11/2000 | Hossainy |
| 6,156,062 A | 12/2000 | McGuinness |
| 6,197,048 B1 | 3/2001 | Richter |
| 6,206,915 B1 | 3/2001 | Fagan |
| 6,240,616 B1 | 6/2001 | Yan |
| 6,241,762 B1 | 6/2001 | Shanley |
| 6,249,952 B1 | 6/2001 | Ding |
| 6,254,632 B1 | 7/2001 | Wu |
| 6,257,706 B1 | 7/2001 | Ahn |
| 6,273,908 B1 | 8/2001 | Ndondo-Lay |
| 6,273,913 B1 | 8/2001 | Wright |
| 6,290,673 B1 | 9/2001 | Shanley |
| 6,293,967 B1 | 9/2001 | Shanley |
| 6,299,604 B1 | 10/2001 | Ragheb |
| 6,299,755 B1 | 10/2001 | Richter |
| 6,306,166 B1 | 10/2001 | Barry |
| 6,331,189 B1 | 12/2001 | Wolinsky |
| 6,334,807 B1 | 1/2002 | Lebel |
| 6,334,871 B1 | 1/2002 | Dor |
| 6,369,355 B1 | 4/2002 | Saunders |
| 6,375,826 B1 | 4/2002 | Wang |
| 6,378,988 B1 | 4/2002 | Taylor |
| 6,379,381 B1 | 4/2002 | Hossainy |
| 6,395,326 B1 | 5/2002 | Castro |
| 6,423,092 B2 | 7/2002 | Datta |
| 6,482,166 B1 | 11/2002 | Fariabi |
| 6,497,916 B1 | 12/2002 | Taylor |
| 6,506,437 B1 | 1/2003 | Harish |
| 6,537,256 B2 | 3/2003 | Santini, Jr. |
| 6,544,582 B1 | 4/2003 | Yoe |
| 6,548,308 B2 | 4/2003 | Ellson et al. |
| 6,551,838 B2 | 4/2003 | Santini, Jr. |
| 6,558,733 B1 | 5/2003 | Hossainy et al. |
| 6,562,065 B1 | 5/2003 | Shanley |
| 6,565,602 B2 | 5/2003 | Rolando |
| 6,585,764 B2 | 7/2003 | Wright |
| 6,599,415 B1 | 7/2003 | Ku |
| 6,616,765 B1 | 9/2003 | Castro et al. |
| 6,635,082 B1 | 10/2003 | Hossainy |
| 6,645,547 B1 | 11/2003 | Shekalim |
| 6,656,162 B2 | 12/2003 | Santini, Jr. |
| 6,676,987 B2 | 1/2004 | Zhong |
| 6,679,980 B1 | 1/2004 | Andreacchi |
| 6,682,771 B2 | 1/2004 | Zhong |
| 6,689,159 B2 | 2/2004 | Lau et al. |
| 6,699,281 B2 | 3/2004 | Vallana |
| 6,723,373 B1 | 4/2004 | Narayanan |
| 6,730,064 B2 | 5/2004 | Ragheb |
| 6,730,116 B1 | 5/2004 | Wolinsky |
| 6,746,686 B2 | 6/2004 | Hughes |
| 6,752,829 B2 | 6/2004 | Kocur |
| 6,758,859 B1 | 7/2004 | Dang |
| 6,764,507 B2 | 7/2004 | Shanley et al. |
| 6,774,278 B1 | 8/2004 | Ragheb |
| 6,776,796 B2 | 8/2004 | Falotico et al. |
| 6,783,543 B2 | 8/2004 | Jang |
| 6,783,793 B1 | 8/2004 | Hossainy |
| 6,790,228 B2 | 9/2004 | Hossainy |
| 6,805,898 B1 | 10/2004 | Wu |
| 6,808,536 B2 | 10/2004 | Wright |
| 6,818,063 B1 | 11/2004 | Kerrigan |
| 6,849,089 B2 | 2/2005 | Stoll |
| 6,852,123 B2 | 2/2005 | Brown |
| 6,855,125 B2 | 2/2005 | Shanley |
| 6,860,946 B2 | 3/2005 | Hossainy |
| 6,861,088 B2 | 3/2005 | Weber |
| 6,863,685 B2 | 3/2005 | Davila |
| 6,865,810 B2 | 3/2005 | Stinson |
| 6,866,810 B2 | 3/2005 | Ahmed |
| 6,867,389 B2 | 3/2005 | Shapovalov |
| 6,887,510 B2 | 5/2005 | Villareal |
| 6,927,359 B2 | 8/2005 | Kleine |
| 6,929,660 B1 | 8/2005 | Ainsworth |
| 6,948,223 B2 | 9/2005 | Shortt |
| 6,955,723 B2 | 10/2005 | Pacetti |
| 6,957,152 B1 | 10/2005 | Esbeck |
| 6,981,985 B2 | 2/2006 | Brown |
| 7,037,552 B2 | 5/2006 | Zhong |
| 7,056,338 B2 | 6/2006 | Shanley |
| 2001/0027291 A1 | 10/2001 | Shanley |
| 2001/0027340 A1 | 10/2001 | Wright |
| 2001/0029351 A1 | 10/2001 | Falotico |
| 2002/0007209 A1 | 1/2002 | Scheerder |
| 2002/0010507 A1 | 1/2002 | Ehr |
| 2002/0013619 A1 | 1/2002 | Shanley |
| 2002/0028243 A1 | 3/2002 | Masters |
| 2002/0032414 A1 | 3/2002 | Ragheb |
| 2002/0038145 A1 | 3/2002 | Jang |
| 2002/0038146 A1 | 3/2002 | Harry |
| 2002/0068969 A1 | 6/2002 | Shanley |
| 2002/0082680 A1 | 6/2002 | Shanley |
| 2002/0107563 A1 | 8/2002 | Shanley |
| 2002/0155212 A1 | 10/2002 | Hossainy |
| 2002/0165604 A1 | 11/2002 | Shanley |
| 2003/0009214 A1 | 1/2003 | Shanley |
| 2003/0028244 A1 | 2/2003 | Bates |
| 2003/0036794 A1 | 2/2003 | Ragheb |
| 2003/0060877 A1 | 3/2003 | Falotico |
| 2003/0068355 A1 | 4/2003 | Shanley |
| 2003/0088307 A1 | 5/2003 | Shulze |
| 2003/0100865 A1 | 5/2003 | Santini |
| 2003/0105511 A1 | 6/2003 | Welsh |
| 2003/0125803 A1 | 7/2003 | Vallana |
| 2003/0157241 A1 | 8/2003 | Hossainy |
| 2003/0167085 A1 | 9/2003 | Shanley |
| 2003/0176915 A1 | 9/2003 | Wright |
| 2003/0199970 A1 | 10/2003 | Shanley |
| 2003/0216699 A1 | 11/2003 | Falotico |
| 2003/0225420 A1 | 12/2003 | Wardle |
| 2004/0006382 A1 | 1/2004 | Sohier |
| 2004/0024449 A1 | 2/2004 | Boyle |
| 2004/0122505 A1 | 6/2004 | Shanley |
| 2004/0127976 A1 | 7/2004 | Diaz |
| 2004/0127977 A1 | 7/2004 | Shanley |
| 2004/0142014 A1 | 7/2004 | Litvack |
| 2004/0143321 A1 | 7/2004 | Litvack |
| 2004/0143322 A1 | 7/2004 | Litvack |
| 2004/0144506 A1 | 7/2004 | Walter |
| 2004/0166140 A1 | 8/2004 | Santini |
| 2004/0193255 A1 | 9/2004 | Shanley |
| 2004/0202692 A1 | 10/2004 | Shanley |
| 2004/0204756 A1 | 10/2004 | Diaz |
| 2004/0220660 A1 | 11/2004 | Shanley |
| 2004/0220665 A1 | 11/2004 | Hossainy |
| 2004/0225350 A1 | 11/2004 | Shanley |
| 2004/0249449 A1 | 12/2004 | Shanley |
| 2005/0058684 A1 | 3/2005 | Shanley |
| 2005/0060020 A1 | 3/2005 | Jenson |
| 2005/0061771 A1 | 3/2005 | Murphy |
| 2005/0064088 A1 | 3/2005 | Fredrickson |
| 2005/0074545 A1 | 4/2005 | Thomas |
| 2005/0075714 A1 | 4/2005 | Cheng |
| 2005/0100577 A1* | 5/2005 | Parker et al. ............ 424/423 |

| | | | |
|---|---|---|---|
| 2005/0106210 A1 | 5/2005 | Ding | |
| 2005/0160891 A1 | 7/2005 | Koch | |
| 2005/0166389 A1 | 8/2005 | Perreault | |
| 2005/0222676 A1 | 10/2005 | Shanley | |
| 2005/0229670 A1 | 10/2005 | Perreault | |
| 2005/0233062 A1 | 10/2005 | Hossainy | |
| 2005/0234538 A1 | 10/2005 | Litvack | |
| 2005/0234544 A1 | 10/2005 | Shanley | |
| 2005/0240256 A1 | 10/2005 | Austin | |
| 2005/0273161 A1 | 12/2005 | Malik | |
| 2005/0278016 A1 | 12/2005 | Welsh | |
| 2006/0008503 A1 | 1/2006 | Shanley | |
| 2006/0009838 A1 | 1/2006 | Shanley | |
| 2006/0030931 A1 | 2/2006 | Shanley | |
| 2006/0064157 A1 | 3/2006 | Shanley | |
| 2006/0096660 A1 | 5/2006 | Diaz | |
| 2006/0122688 A1 | 6/2006 | Shanley | |
| 2006/0122697 A1 | 6/2006 | Shanley | |
| 2006/0177564 A1 | 8/2006 | Diaz | |
| 2006/0178735 A1 | 8/2006 | Litvack | |

FOREIGN PATENT DOCUMENTS

| | | |
|---|---|---|
| EP | 540290 | 5/1993 |
| EP | 734699 | 10/1996 |
| EP | 747069 | 12/1996 |
| EP | 770401 | 5/1997 |
| EP | 846447 | 6/1998 |
| EP | 853927 | 7/1998 |
| EP | 950386 | 10/1999 |
| EP | 956832 | 11/1999 |
| EP | 968013 | 1/2000 |
| EP | 973462 | 1/2000 |
| EP | 1132058 | 9/2001 |
| EP | 1172074 | 1/2002 |
| EP | 1181903 | 2/2002 |
| EP | 1222941 | 7/2002 |
| EP | 1341479 | 9/2003 |
| EP | 1493456 | 1/2005 |
| EP | 1498084 | 1/2005 |
| EP | 875218 | 2/2005 |
| EP | 1518570 | 3/2005 |
| EP | 1527754 | 5/2005 |
| EP | 1559439 | 8/2005 |
| EP | 1561436 | 8/2005 |
| EP | 1582180 | 10/2005 |
| EP | 1600180 | 11/2005 |
| EP | 1277449 | 6/2006 |
| WO | WO9823228 | 6/1998 |
| WO | WO9833546 | 8/1998 |
| WO | WO9836784 | 8/1998 |
| WO | WO9916386 | 4/1999 |
| WO | WO9923977 | 5/1999 |
| WO | WO9937245 | 7/1999 |
| WO | WO9949928 | 10/1999 |
| WO | WO0010622 | 3/2000 |
| WO | WO0117577 | 3/2001 |
| WO | WO0226162 | 4/2002 |
| WO | WO0226281 | 4/2002 |
| WO | WO0232347 | 4/2002 |
| WO | WO0243788 | 6/2002 |
| WO | WO02060506 | 8/2002 |
| WO | WO02087586 | 11/2002 |
| WO | WO03015664 | 2/2003 |
| WO | WO03035134 | 5/2003 |
| WO | WO03077730 | 9/2003 |
| WO | WO2004043509 | 5/2004 |
| WO | WO2004043510 | 5/2004 |
| WO | WO2004043511 | 5/2004 |
| WO | WO2004087015 | 10/2004 |
| WO | WO2004094096 | 11/2004 |
| WO | WO2004096093 | 11/2004 |
| WO | WO2004096176 | 11/2004 |
| WO | WO2004096311 | 11/2004 |
| WO | WO2005004945 | 1/2005 |
| WO | WO2005016187 | 2/2005 |
| WO | WO2005016396 | 2/2005 |
| WO | WO2005018606 | 3/2005 |
| WO | WO2005027794 | 3/2005 |
| WO | WO2005034805 | 4/2005 |
| WO | WO2005034806 | 4/2005 |
| WO | WO2005037444 | 4/2005 |
| WO | WO2005037447 | 4/2005 |
| WO | WO2005046521 | 5/2005 |
| WO | WO2005047572 | 5/2005 |
| WO | WO2005089951 | 9/2005 |
| WO | WO2005092420 | 10/2005 |
| WO | WO2005102590 | 11/2005 |
| WO | WO2005112570 | 12/2005 |
| WO | WO2005115277 | 12/2005 |
| WO | WO2005120397 | 12/2005 |
| WO | WO2006007473 | 1/2006 |
| WO | WO2006012034 | 2/2006 |
| WO | WO2006012060 | 2/2006 |

OTHER PUBLICATIONS

Serruys, P.W. et al. "The Effect of Variable Dose and Release Kinetics on Neointimal Hyperplasia Using a Novel Paclitaxel-Eluting Stent Platform", Journal of the American College of Cardiology, vol. 46, No. 2, 2005, pp. 253-260.

* cited by examiner

EXPANDABLE MEDICAL DEVICE WITH OPENINGS FOR DELIVERY OF MULTIPLE BENEFICIAL AGENTS

CROSS REFERENCE TO RELATED APPLICATIONS

This application is a Continuation-in-Part of U.S. patent application Ser. No. 10/668,430, filed on Sep. 22, 2003, which application claims priority under 35 U.S.C. §119(e) to U.S. Provisional Application Ser. No. 60/412,489 filed Sep. 20, 2002, both of which are incorporated herein by reference in their entirety.

BACKGROUND OF THE INVENTION

1. Field of the Invention

The present invention relates to tissue-supporting medical devices, and more particularly to expandable, non-removable devices that are implanted within a bodily lumen of a living animal or human to support the organ and maintain patency, and that have openings for delivery of a plurality of beneficial agents to the intervention site.

2. Summary of the Related Art

In the past, permanent or biodegradable devices have been developed for implantation within a body passageway to maintain patency of the passageway. These devices are typically introduced percutaneously, and transported transluminally until positioned at a desired location. These devices are then expanded either mechanically, such as by the expansion of a mandrel or balloon positioned inside the device, or expand themselves by releasing stored energy upon actuation within the body. Once expanded within the lumen, these devices, called stents, become encapsulated within the body tissue and remain a permanent implant.

Known stent designs include monofilament wire coil stents (U.S. Pat. No. 4,969,458); welded metal cages (U.S. Pat. Nos. 4,733,665 and 4,776,337); and, most prominently, thin-walled metal cylinders with axial slots formed around the circumference (U.S. Pat. Nos. 4,733,665; 4,739,762; and 4,776,337). Known construction materials for use in stents include polymers, organic fabrics and biocompatible metals, such as, stainless steel, gold, silver, tantalum, titanium, and shape memory alloys, such as Nitinol.

U.S. Pat. No. 6,241,762 which is incorporated herein by reference in its entirety discloses a non-prismatic stent design which remedies several performance deficiencies of previous stents. In addition, preferred embodiments of this patent provide a stent with large, non-deforming strut and link elements, which can contain holes without compromising the mechanical properties of the strut or link elements, or the device as a whole. Further, these holes may serve as large, protected reservoirs for delivering various beneficial agents to the device implantation site without the need for a surface coating on the stent.

Of the many problems that may be addressed through stent-based local delivery of beneficial agents, one of the most important is restenosis. Restenosis is a major complication that can arise following vascular interventions such as angioplasty and the implantation of stents. Simply defined, restenosis is a wound healing process that reduces the vessel lumen diameter by extracellular matrix deposition and vascular smooth muscle cell proliferation and which may ultimately result in renarrowing or even reocclusion of the lumen. Despite the introduction of improved surgical techniques, devices and pharmaceutical agents, the overall restenosis rate for bare metal stents is still reported in the range of 25% to 50% within six to twelve months after an angioplasty procedure. To treat this condition, additional revascularization procedures are frequently required, thereby increasing trauma and risk to the patient.

Conventional stents with surface coatings of various beneficial agents have shown promising results in reducing restenosis. U.S. Pat. No. 5,716,981, for example, discloses a stent that is surface-coated with a composition comprising a polymer carrier and paclitaxel (a well-known compound that is commonly used in the treatment of cancerous tumors). The patent offers detailed descriptions of methods for coating stent surfaces, such as spraying and dipping, as well as the desired character of the coating itself: it should "coat the stent smoothly and evenly" and "provide a uniform, predictable, prolonged release of the anti-angiogenic factor." Surface coatings, however, can provide little actual control over the release kinetics of beneficial agents. These coatings are necessarily very thin, typically 5 to 8 microns deep. The surface area of the stent, by comparison is very large, so that the entire volume of the beneficial agent has a very short diffusion path to discharge into the surrounding tissue. The resulting cumulative drug release profile is characterized by a large initial burst, followed by a rapid approach to an asymptote, rather than the desired "uniform, prolonged release," or linear release.

Increasing the thickness of the surface coating has the beneficial effects of improving drug release kinetics including the ability to better control drug release and to allow increased drug loading. However, the increased coating thickness results in increased overall thickness of the stent wall. This is undesirable for a number of reasons, including increased trauma to the vessel lumen during implantation, reduced flow cross-section of the lumen after implantation, and increased vulnerability of the coating to mechanical failure or damage during expansion and implantation. Coating thickness is one of several factors that affect the release kinetics of the beneficial agent, and limitations on thickness thereby limit the range of release rates, durations, and the like that can be achieved.

Surface coatings also seriously limit the delivery of multiple drugs from a stent. For example, if multiple drugs were to be released from a surface coating, the release rates, delivery periods and other release characteristics cannot be independently controlled. However, restenosis involves multiple biological processes and may be treated most effectively by a combination of drugs selected to act on these different biological processes.

Recent research described in a paper titled "Physiological Transport Forces Govern Drug Distribution for Stent-Based Delivery" by Chao-Wei Hwang et al. has revealed an important interrelationship between the spatial and temporal drug distribution properties of drug eluting stents, and cellular drug transport mechanisms. In pursuit of enhanced mechanical performance and structural properties stent designs have evolved to more complex geometries with inherent inhomogeneity in the circumferential and longitudinal distribution of stent struts. Examples of this trend are the typical commercially available stents which expand to a roughly diamond or hexagonal shape when deployed in a bodily lumen. Both have been used to deliver a beneficial agent in the form of a surface coating. Studies have shown that lumen tissue portions immediately adjacent to the struts acquire much higher concentrations of drug than more remote tissue portions, such as those located in the middle of the "diamond" shaped strut cells. Significantly, this concentration gradient of drug within the lumen wall remains higher over time for hydrophobic beneficial agents, such as paclitaxel or Rapamycin, which have proven to be the most effective anti-proliferatives to date. Because local drug concentrations and gradients are inextricably linked to biological effect, the initial spatial distribution of the beneficial agent sources (the stent struts) is key to efficacy.

In addition to sub-optimal spatial distribution of beneficial agents, there are further problems with surface coated stents. The fixed matrix polymer carriers frequently used in the device coatings typically retain approximately 30% of the beneficial agent in the coating indefinitely. Since these beneficial agents are frequently highly cytotoxic, sub-acute and chronic problems such as chronic inflammation, late thrombosis, and late or incomplete healing of the vessel wall may occur. Additionally, the carrier polymers themselves are often inflammatory to the tissue of the vessel wall. On the other hand, use of bio-degradable polymer carriers on stent surfaces can result in "mal-apposition" or voids between the stent and tissue of the vessel wall after the polymer carrier has degraded. The voids permit differential motion between the stent and adjacent tissue. Resulting problems include micro-abrasion and inflammation, stent drift, and failure to re-endothelialize the vessel wall.

Early human clinical trials suggest that there may be further problems with first generation drug delivery devices. Follow-up examination of clinical trial patients at 6 to 18 months after drug coated stent implantation indicates that mal-apposition of stent struts to arterial walls and edge effect restenosis may occur in significant numbers of patients. Edge effect restenosis occurs just beyond the proximal and distal edges of the stent and progresses around the stent edges and into the interior (luminal) space, frequently requiring repeat revascularization of the patient.

Another significant problem is that expansion of the stent may stress an overlying polymeric coating causing the coating to peel, crack, or rupture which may effect drug release kinetics or have other untoward effects. These effects have been observed in first generation drug coated stents when these stents are expanded to larger diameters, preventing their use thus far in larger diameter arteries. Further, expansion of such a coated stent in an atherosclerotic blood vessel will place circumferential shear forces on the polymeric coating, which may cause the coating to separate from the underlying stent surface. Such separation may again have untoward effects including embolization of coating fragments causing vascular obstruction.

SUMMARY OF THE INVENTION

In view of the drawbacks of the prior art, it would be advantageous to provide a stent capable of delivering a relatively large volume of a beneficial agent to a traumatized site in a vessel lumen while avoiding the numerous problems associated with surface coatings containing beneficial agents, without increasing the effective wall thickness of the stent, and without adversely impacting the mechanical expansion properties of the stent.

It would further be advantageous to provide a tissue supporting device with different beneficial agents provided in different holes to achieve a desired spatial distribution of two or more beneficial agents.

It would further be advantageous to provide a tissue supporting device with different beneficial agents provided in different holes to achieve a desired different release kinetic for two different beneficial agents from the same device.

In accordance with one aspect of the present invention, an expandable medical device for delivery of a beneficial agent comprises a substantially cylindrical device which is expandable from a cylinder having a first diameter to a cylinder having a second diameter; a first plurality of openings formed in the substantially cylindrical device containing a first beneficial agent for delivery to tissue, wherein the first beneficial agent is arranged to be delivered according to a first release curve to target a first biological process of restenosis; and a second plurality of openings formed in the substantially cylindrical device containing a second beneficial agent for delivery to tissue. The second beneficial agent is arranged to be delivered according to a second release curve different from the first release curve to target a second biological process of restenosis.

In accordance with an additional aspect of the present invention, a method of reducing restenosis in a body passageway comprises the steps of positioning a tissue supporting device in a body passageway to support the tissue, the tissue supporting device containing a first and a second beneficial agent in openings in the device and delivering the first and second beneficial agents to tissue adjacent the tissue supporting device to treat restenosis by two different mechanisms of action.

In accordance with a further aspect of the present invention, an expandable medical device for delivery of a beneficial agent comprises a substantially cylindrical device which is expandable from a cylinder having a first diameter to a cylinder having a second diameter; a first plurality of openings formed in the substantially cylindrical device containing a first beneficial agent for delivery to tissue, wherein the first beneficial agent is arranged to be delivered according to a first release curve to target a restenosis; and a second plurality of openings formed in the substantially cylindrical device containing a second beneficial agent for delivery to tissue. The second beneficial agent is arranged to be delivered according to a second release curve different from the first release curve to target a disease other than restenosis.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF THE PREFERRED EMBODIMENTS

Figure 1:
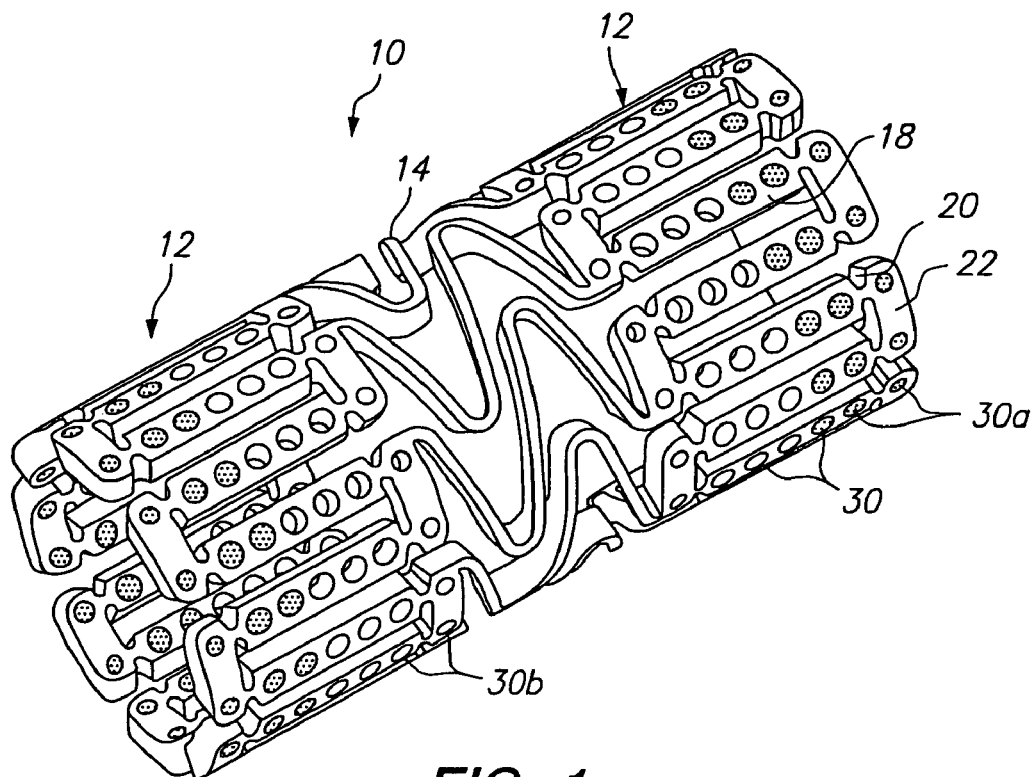
FIG. 1 is an isometric view of an expandable medical device with a beneficial agent at the ends.

FIG. 1 illustrates an expandable medical device having a plurality of holes containing a beneficial agent for delivery to tissue by the expandable medical device. The expandable medical device 10 shown in FIG. 1 is cut from a tube of material to form a cylindrical expandable device. The expandable medical device 10 includes a plurality of cylindrical sections 12 interconnected by a plurality of bridging elements 14. The bridging elements 14 allow the tissue supporting device to bend axially when passing through the torturous path of vasculature to a deployment site and allow the device to bend axially when necessary to match the curvature of a lumen to be supported. Each of the cylindrical tubes 12 is formed by a network of elongated struts 18 which are interconnected by ductile hinges 20 and circumferential struts 22. During expansion of the medical device 10 the ductile hinges 20 deform while the struts 18 are not deformed. Further details of one example of the expandable medical device are described in U.S. Pat. No. 6,241,762 which is incorporated herein by reference in its entirety.

As shown in FIG. 1, the elongated struts 18 and circumferential struts 22 include openings 30, some of which contain a beneficial agent for delivery to the lumen in which the expandable medical device is implanted. In addition, other portions of the device 10, such as the bridging elements 14, may include openings, as discussed below with respect to FIG. 5. Preferably, the openings 30 are provided in non-deforming portions of the device 10, such as the struts 18, so that the openings are non-deforming and the beneficial agent is delivered without risk of being fractured, expelled, or otherwise damaged during expansion of the device. A further description of one example of the manner in which the beneficial agent may be loaded within the openings 30 is described in U.S. patent application Ser. No. 09/948,987, filed Sep. 7, 2001, which is incorporated herein by reference in its entirety.

The embodiments of the invention shown can be further refined by using Finite Element Analysis and other techniques to optimize the deployment of the beneficial agents within the openings 30. Basically, the shape and location of the openings 30, can be modified to maximize the volume of the voids while preserving the relatively high strength and rigidity of the struts with respect to the ductile hinges 20. According to one preferred embodiment of the present invention, the openings have an area of at least $5 \times 10^{-6}$ square inches, and preferably at least $7 \times 10^{-6}$ square inches. Typically, the openings are filled about 50% to about 95% full of beneficial agent.

DEFINITIONS

The terms "agent" or "beneficial agent" as used herein are intended to have the broadest possible interpretation and are used to include any therapeutic agent or drug, as well as inactive agents such as barrier layers, carrier layers, therapeutic layers, or protective layers.

The terms "drug" and "therapeutic agent" are used interchangeably to refer to any therapeutically active substance that is delivered to a bodily lumen of a living being to produce a desired, usually beneficial, effect. Beneficial agents may include one or more drug or therapeutic agent.

The present invention is particularly well suited for the delivery of antineoplastics, antiangiogenics, angiogenic factors, anti-inflammatories, immuno-suppressants, antirestenotics, antiplatelet agents, vasodilators, anti-thrombotics, antiproliferatives, such as paclitaxel and Rapamycin, for example, and antithrombins, such as heparin, for example.

The term "erosion" means the process by which components of a medium or matrix are bioresorbed and/or degraded and/or broken down by chemical or physical processes. For example in reference to biodegradable polymer matrices, erosion can occur by cleavage or hydrolysis of the polymer chains, thereby increasing the solubility of the matrix and suspended beneficial agents.

The term "erosion rate" is a measure of the amount of time it takes for the erosion process to occur, usually reported in unit-area per unit-time.

The terms "matrix" or "bioresorbable matrix" are used interchangeably to refer to a medium or material that, upon implantation in a subject, does not elicit a detrimental response sufficient to result in the rejection of the matrix. The matrix typically does not provide any therapeutic responses itself, though the matrix may contain or surround a beneficial agent, as defined herein. A matrix is also a medium that may simply provide support, structural integrity or structural barriers. The matrix may be polymeric, non-polymeric, hydrophobic, hydrophilic, lipophilic, amphiphilic, and the like.

The term "openings" includes both through openings and recesses.

The term "pharmaceutically acceptable" refers to the characteristic of being non-toxic to a host or patient and suitable for maintaining the stability of a beneficial agent and allowing the delivery of the beneficial agent to target cells or tissue.

The term "polymer" refers to molecules formed from the chemical union of two or more repeating units, called monomers. Accordingly, included within the term "polymer" may be, for example, dimers, trimers and oligomers. The polymer may be synthetic, naturally-occurring or semisynthetic. In preferred form, the term "polymer" refers to molecules which typically have a $M_W$ greater than about 3000 and preferably greater than about 10,000 and a $M_W$ that is less than about 10 million, preferably less than about a million and more preferably less than about 200,000. Examples of polymers include but are not limited to, poly-α-hydroxy acid esters such as, polylactic acid (PLLA or DLPLA), polyglycolic acid, polylactic-co-glycolic acid (PLGA), polylactic acid-co-caprolactone; poly (block-ethylene oxide-block-lactide-co-glycolide) polymers (PEO-block-PLGA and PEO-block-PLGA-block-PEO); polyethylene glycol and polyethylene oxide, poly (block-ethylene oxide-block-propylene oxide-block-ethylene oxide); polyvinyl pyrrolidone; polyorthoesters; polysaccharides and polysaccharide derivatives such as polyhyaluronic acid, poly (glucose), polyalginic acid, chitin, chitosan, chitosan derivatives, cellulose, methyl cellulose, hydroxyethylcellulose, hydroxypropylcellulose, carboxymethylcellulose, cyclodextrins and substituted cyclodextrins, such as beta-cyclodextrin sulfobutyl ethers; polypeptides and proteins, such as polylysine, polyglutamic acid, albumin; polyanhydrides; polyhydroxy alkonoates such as polyhydroxy valerate, polyhydroxy butyrate, and the like.

The term "primarily" with respect to directional delivery, refers to an amount greater than about 50% of the total amount of therapeutic agent provided to a blood vessel is provided in the primary direction.

The various embodiments of the invention described herein provide different beneficial agents in different openings in the expandable device or beneficial agent in some openings and not in others. The particular structure of the expandable medical device may be varied without departing from the invention. Since each opening is filled independently, individual chemical compositions and pharmacokinetic properties can be imparted to the beneficial agent in each opening.

One example of the use of different beneficial agents in different openings in an expandable medical device or beneficial agents in some openings and not in others, is in addressing edge effect restenosis. As discussed above, current generation coated stents have a significant problem with edge effect restenosis or restenosis occurring just beyond the edges of the stent and progressing around the stent and into the interior luminal space.

The causes of edge effect restenosis in first generation drug delivery stents are currently not well understood. It may be that the region of tissue injury due to angioplasty and/or stent implantation extends beyond the diffusion range of current generation beneficial agents such as paclitaxel and Rapamycin, which tend to partition strongly in tissue. A similar phenomenon has been observed in radiation therapies in which low doses of radiation at the edges of stent have proven stimulatory in the presence of an injury. In this case, radiating over a longer length until uninjured tissue is irradiated solved the problem. In the case of drug delivery stents, placing higher doses or higher concentrations of beneficial agents along the stent edges, placing different agents at the stent edges which diffuse more readily through the tissue, or placing different beneficial agents or combinations of beneficial agents at the edges of the device would help to remedy the edge effect restenosis problem.

FIG. 1 illustrates an expandable medical device 10 with "hot ends" or beneficial agent provided in the openings 30a at the ends of the device in order to treat and reduce edge effect restenosis. The remaining openings 30b in the central portion of the device may be empty (as shown) or may contain a lower concentration of beneficial agent.

Other mechanisms of edge effect restenosis may involve cytotoxicity of particular drugs or combinations of drugs. Such mechanisms could include a physical or mechanical contraction of tissue similar to that seen in epidermal scar tissue formation, and the stent might prevent the contractile response within its own boundaries, but not beyond its edges. Further, the mechanism of this latter form of restenosis may be related to sequelae of sustained or local drug delivery to the arterial wall that is manifest even after the drug itself is no longer present in the wall. That is, the restenosis may be a response to a form of noxious injury related to the drug and/or the drug carrier. In this situation, it might be beneficial to exclude certain agents from the edges of the device.

Figure 2:
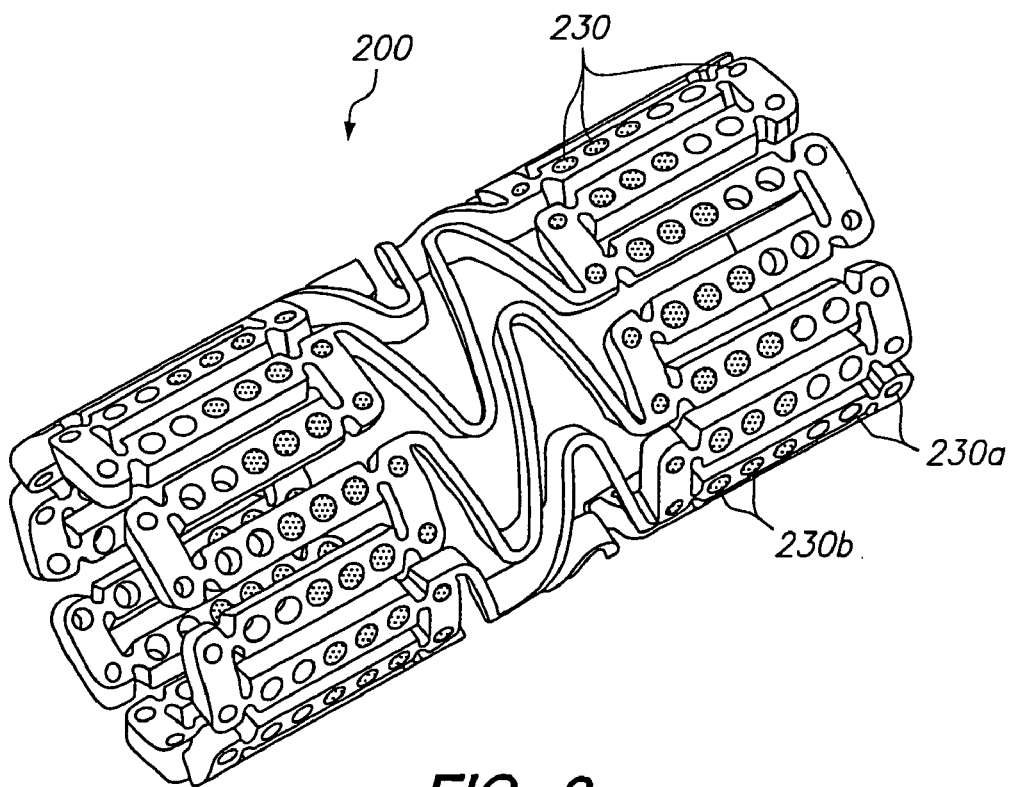
FIG. 2 is an isometric view of an expandable medical device with a beneficial agent at a central portion and no beneficial agent at the ends.

FIG. 2 illustrates an alternative embodiment of an expandable medical device 200 having a plurality of openings 230 in which the openings 230b in a central portion of the device are filled with a beneficial agent and the openings 230a at the edges of the device remain empty. The device of FIG. 2 is referred to as having "cool ends".

In addition to use in reducing edge effect restenosis, the expandable medical device 200 of FIG. 2 may be used in conjunction with the expandable medical device 10 of FIG. 1 or another drug delivery stent when an initial stenting procedure has to be supplemented with an additional stent. For example, in some cases the device 10 of FIG. 1 with "hot ends" or a device with uniform distribution of drug may be implanted improperly. If the physician determines that the device does not cover a sufficient portion of the lumen a supplemental device may be added at one end of the existing device and slightly overlapping the existing device. When the supplemental device is implanted, the device 200 of FIG. 2 is used so that the "cool ends" of the medical device 200 prevent double-dosing of the beneficial agent at the overlapping portions of the devices 10, 200.

Figure 3:
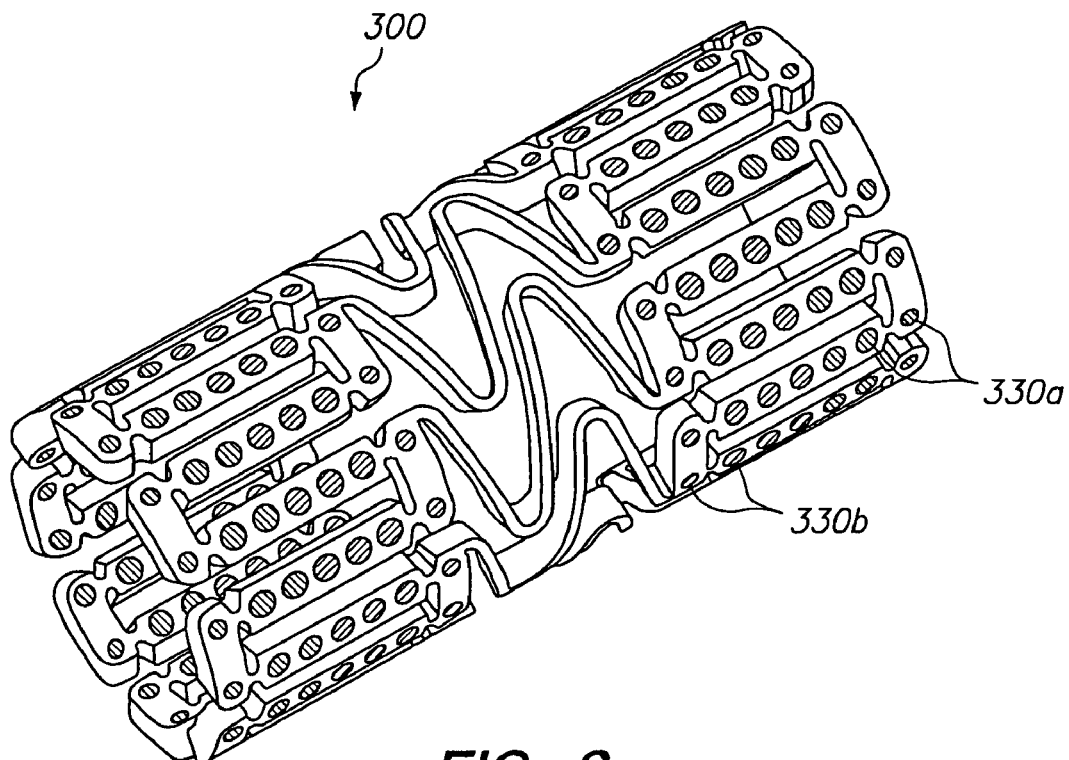
FIG. 3 is an isometric view of an expandable medical device with different beneficial agents in different holes.

FIG. 3 illustrates a further alternative embodiment of the invention in which different beneficial agents are positioned in different holes of an expandable medical device 300. A first beneficial agent is provided in holes 330a at the ends of the device and a second beneficial agent is provided in holes 330b at a central portion of the device. The beneficial agent may contain different drugs, the same drugs in different concentrations, or different variations of the same drug. The embodiment of FIG. 3 may be used to provide an expandable medical device 300 with either "hot ends" or "cool ends."

Preferably, each end portion of the device 300 which includes the holes 330a containing the first beneficial agent extends at least one hole and up to about 15 holes from the edge. This distance corresponds to about 0.005 to about 0.1 inches from the edge of an unexpanded device. The distance from the edge of the device 300 which includes the first beneficial agent is preferably about one section, where a section is defined between the bridging elements.

Different beneficial agents containing different drugs may be disposed in different openings in the stent. This allows the delivery of two or more beneficial agents from a single stent in any desired delivery pattern. Alternatively, different beneficial agents containing the same drug in different concentrations may be disposed in different openings. This allows the drug to be uniformly distributed to the tissue with a non-uniform device structure.

The two or more different beneficial agents provided in the devices described herein may contain (1) different drugs; (2) different concentrations of the same drug; (3) the same drug with different release kinetics, i.e., different matrix erosion rates; or (4) different forms of the same drug. Examples of different beneficial agents formulated containing the same drug with different release kinetics may use different carriers to achieve the elution profiles of different shapes. Some examples of different forms of the same drug include forms of a drug having varying hydrophilicity or lipophilicity.

In one example of the device 300 of FIG. 3, the holes 330a at the ends of the device are loaded with a first beneficial agent comprising a drug with a high lipophilicity while holes 330b at a central portion of the device are loaded with a second beneficial agent comprising the drug with a lower lipophilicity. The first high lipophilicity beneficial agent at the "hot ends" will diffuse more readily into the surrounding tissue reducing the edge effect restenosis.

The device 300 may have an abrupt transition line at which the beneficial agent changes from a first agent to a second agent. For example, all openings within 0.05 inches of the end of the device may contain the first agent while the remaining openings contain the second agent. Alternatively, the device may have a gradual transition between the first agent and the second agent. For example, a concentration of the drug in the openings can progressively increase (or decrease) toward the ends of the device. In another example, an amount of a first drug in the openings increases while an amount of a second drug in the openings decreases moving toward the ends of the device.

Figure 4:
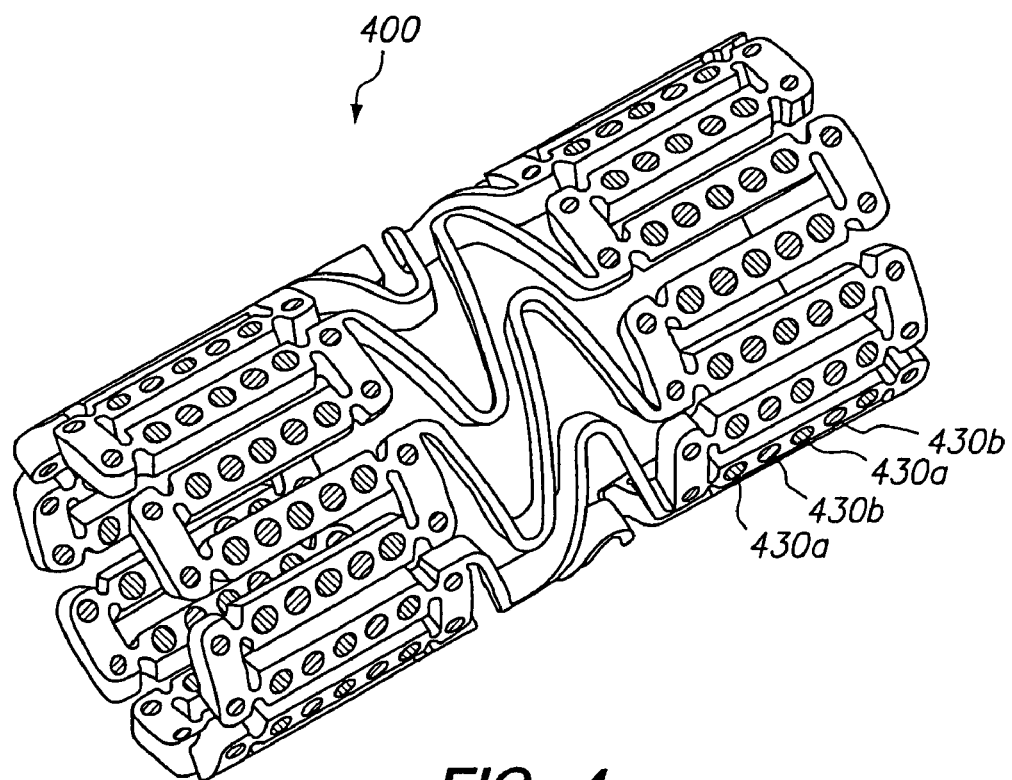
FIG. 4 is an isometric view of an expandable medical device with different beneficial agents in alternating holes.

FIG. 4 illustrates a further alternative embodiment of an expandable medical device 400 in which different beneficial agents are positioned in different openings 430a, 430b in the device in an alternating or interspersed manner. In this manner, multiple beneficial agents can be delivered to tissue over the entire area or a portion of the area supported by the device. This embodiment will be useful for delivery of multiple beneficial agents where combination of the multiple agents into a single composition for loading in the device is not possible due to interactions or stability problems between the beneficial agents.

In addition to the use of different beneficial agents in different openings to achieve different drug concentrations at different defined areas of tissue, the loading of different beneficial agents in different openings may be used to provide a more even spatial distribution of the beneficial agent delivered in instances where the expandable medical device has a non-uniform distribution of openings in the expanded configuration.

The use of different drugs in different openings in an interspersed or alternating manner allows the delivery of two different drugs which may not be deliverable if combined within the same polymer/drug matrix composition. For example, the drugs themselves may interact in an undesirable way. Alternatively, the two drugs may not be compatible with the same polymers for formation of the matrix or with the same solvents for delivery of the polymer/drug matrix into the openings.

Further, the embodiment of FIG. 4 having different drugs in different openings in an interspersed arrangement provide the ability to deliver different drugs with very different desired release kinetics from the same medical device or stent and to optimize the release kinetic depending on the mechanism of action and properties of the individual agents. For example, the water solubility of an agent greatly affects the release of the agent from a polymer or other matrix. A highly water soluble compound will generally be delivered very quickly from a polymer matrix, whereas, a lipophilic agent will be delivered over a longer time period from the same matrix. Thus, if a hydrophilic agent and a lipophilic agent are to be delivered as a dual drug combination from a medical device, it is difficult to achieve a desired release profile for these two agents delivered from the same polymer matrix.

The system of FIG. 4 allows the delivery of a hydrophilic and a lipophilic drug easily from the same stent. Further, the system of FIG. 4 allows the delivery two agents at two different release kinetics and/or administration periods. Each of the initial release in the first 24 hours, the release rate following the first 24 hours, the total administration period and any other characteristics of the release of the two drugs can be independently controlled. For example the release rate of the first beneficial agent can be arranged to be delivered with at least 40% (preferably at least 50%) of the drug delivered in the first 24 hours and the second beneficial agent can be arranged to be delivered with less than 20% (preferably less than 10%) of the drug delivered in the first 24 hours. The administration period of the first beneficial agent can be about 3 weeks or less (preferably 2 weeks or less) and the administration period of the second beneficial agent can be about 4 weeks or more.

Restenosis or the recurrence of occlusion post-intervention, involves a combination or series of biological processes. These processes include the activation of platelets and macrophages. Cytokines and growth factors contribute to smooth muscle cell proliferation and upregulation of genes and metalloproteinases lead to cell growth, remodeling of extracellular matrix, and smooth muscle cell migration. A drug therapy which addresses a plurality of these processes by a combination of drugs may be the most successfully antirestenotic therapy. The present invention provides a means to achieve such a successful combination drug therapy.

The examples discussed below illustrate some of the combined drug systems which benefit from the ability to release different drugs in different holes. One example of a beneficial system for delivering two drugs from interspersed or alternating holes is the delivery of an anti-inflammatory agent or an immunosuppressant agent in combination with an antiproliferative agent or an anti-migratory agent. Other combinations of these agents may also be used to target multiple biological processes involved in restenosis. The anti-inflammatory agent mitigates the initial inflammatory response of the vessel to the angioplasty and stenting and is delivered at a high rate initially followed by a slower delivery over a time period of about two weeks to match the peak in the development of macrophages which stimulate the inflammatory response. The antiproliferative agent is delivered at a relatively even rate over a longer time period to reduce smooth muscle cell migration and proliferation.

In addition to the examples which will be given below, the following chart illustrates some of the useful two drug combination therapies which can be achieved by placing the drugs into different openings in the medical device.

|  | PTX | 2-Cda | Epothilone D | Imatinib mesylate Gleevec | Rapamycin analog | Pimecrolimus | PKC-412 | Dexamethasone | Farglitazar | Insulin | VIP | ApoA-I milano |
|---|---|---|---|---|---|---|---|---|---|---|---|---|
| PTX | | x | | x | | x | x | x | | x | x | x |
| 2-CdA | | | x | x | x | x | x | | x | | | |
| Epothilone D | | | | x | | | x | x | | x | x | x |
| Imatinib mesylate Gleevec | | | | | x | x | x | x | | | | |
| Rapamycin analog | | | | | | | x | x | | x | x | x |
| Pimecrolimus | | | | | | | x | x | | x | x | x |
| PKC-412 | | | | | | | | x | | x | x | x |
| Dexamethasone | | | | | | | | | | | x | x |
| Farglitazar | | | | | | | | | | | x | x |
| Insulin | | | | | | | | | | | x | |
| VIP | | | | | | | | | | | | x |
| ApoA-I milano | | | | | | | | | | | | |

The placement of the drugs in different openings allows the release kinetics to be tailored to the particular agent regardless of the hydrophobicity or lipophobicity of the drug. Examples of some arrangements for delivery of a lipophilic drug at a substantially constant or linear release rate are described in WO 04/110302 published on Dec. 23, 2004, which is incorporated herein by reference in its entirety. Examples of some of the arrangements for delivery of hydrophilic drug are described in WO 04/043510, published on May 27, 2004 which is incorporated herein by reference in its entirety. The hydrophilic drugs listed above include CdA, Gleevec, VIP, insulin, and ApoA-1 milano. The lipophilic drugs listed above include paclitaxel, Epothilone D, rapamycin, pimecrolimus, PKC-412 and Dexamethazone. Farglitazar is partly liphophillic and partly hydrophilic.

In addition to the delivery of multiple of drugs to address different biological processes involved in restenosis, the present invention can deliver two different drugs for treatment of different diseases from the same stent. For example, a stent can deliver an anti-proliferative, such as paclitaxel or a limus drug from one set of openings for treatment of restenosis while delivering a myocardial preservative drug, such as insulin, from other openings for the treatment of acute myocardial infarction.

Figure 5:
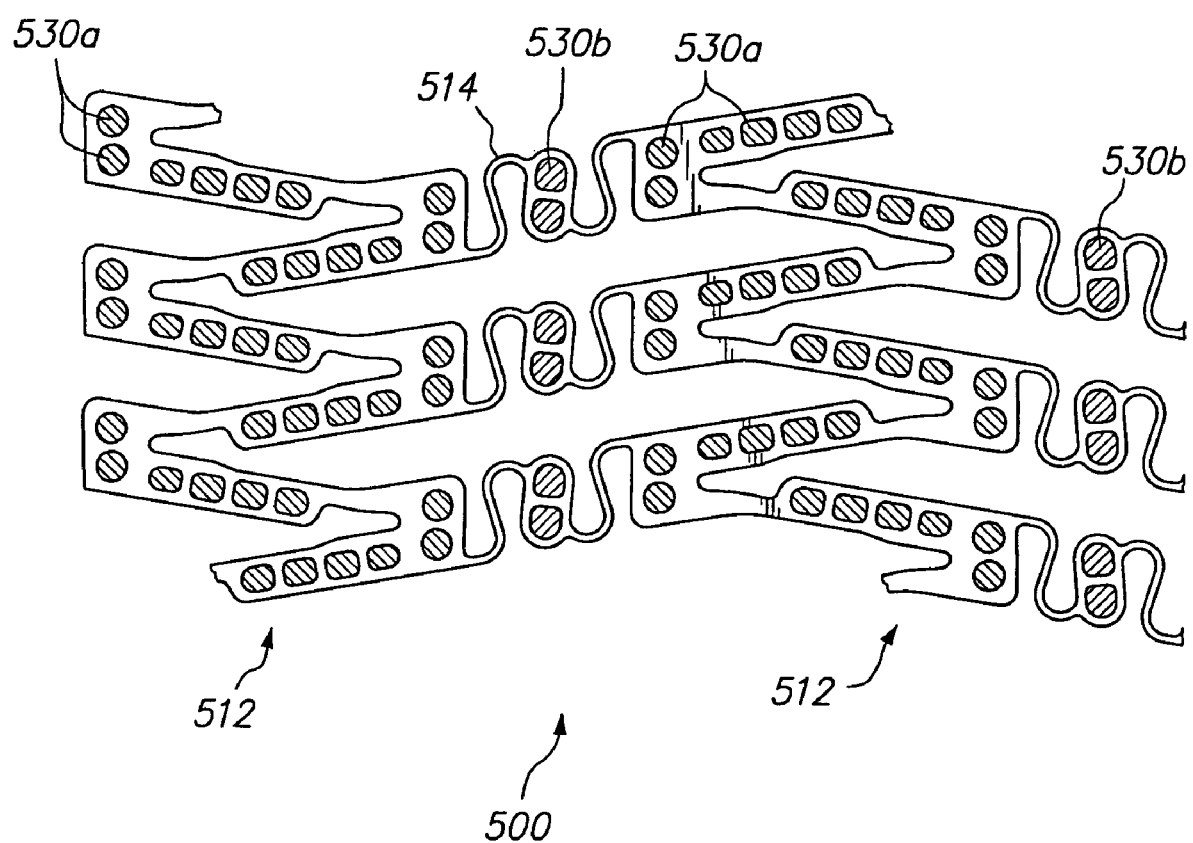
FIG. 5 is an enlarged side view of a portion of an expandable medical device with beneficial agent openings in the bridging elements.

In many of the known expandable devices and for the device illustrated in FIG. 5 the coverage of the device 500 is greater at the cylindrical tube portions 512 of the device than at the bridging elements 514. Coverage is defined as the ratio of the device surface area to the area of the lumen in which the device is deployed. When a device with varying coverage is used to deliver a beneficial agent contained in openings in the device, the beneficial agent concentration delivered to the tissue adjacent the cylindrical tube portions 512 is greater that the beneficial agent delivered to the tissue adjacent the bridging elements 514. In order to address this longitudinal variation in device structure and other variations in device coverage which lead to uneven beneficial agent delivery concentrations, the concentration of the beneficial agent may be varied in the openings at portions of the device to achieve a more even distribution of the beneficial agent throughout the tissue. In the case of the embodiment of FIG. 5, the openings 530a in the tube portions 512 include a beneficial agent with a lower drug concentration than the openings 530b in the bridging elements 514. The uniformity of agent delivery may be achieved in a variety of manners including varying the drug concentration, the opening diameter or shape, the amount of agent in the opening (i.e., the percentage of the opening filed), the matrix material, or the form of the drug.

Figure 6:
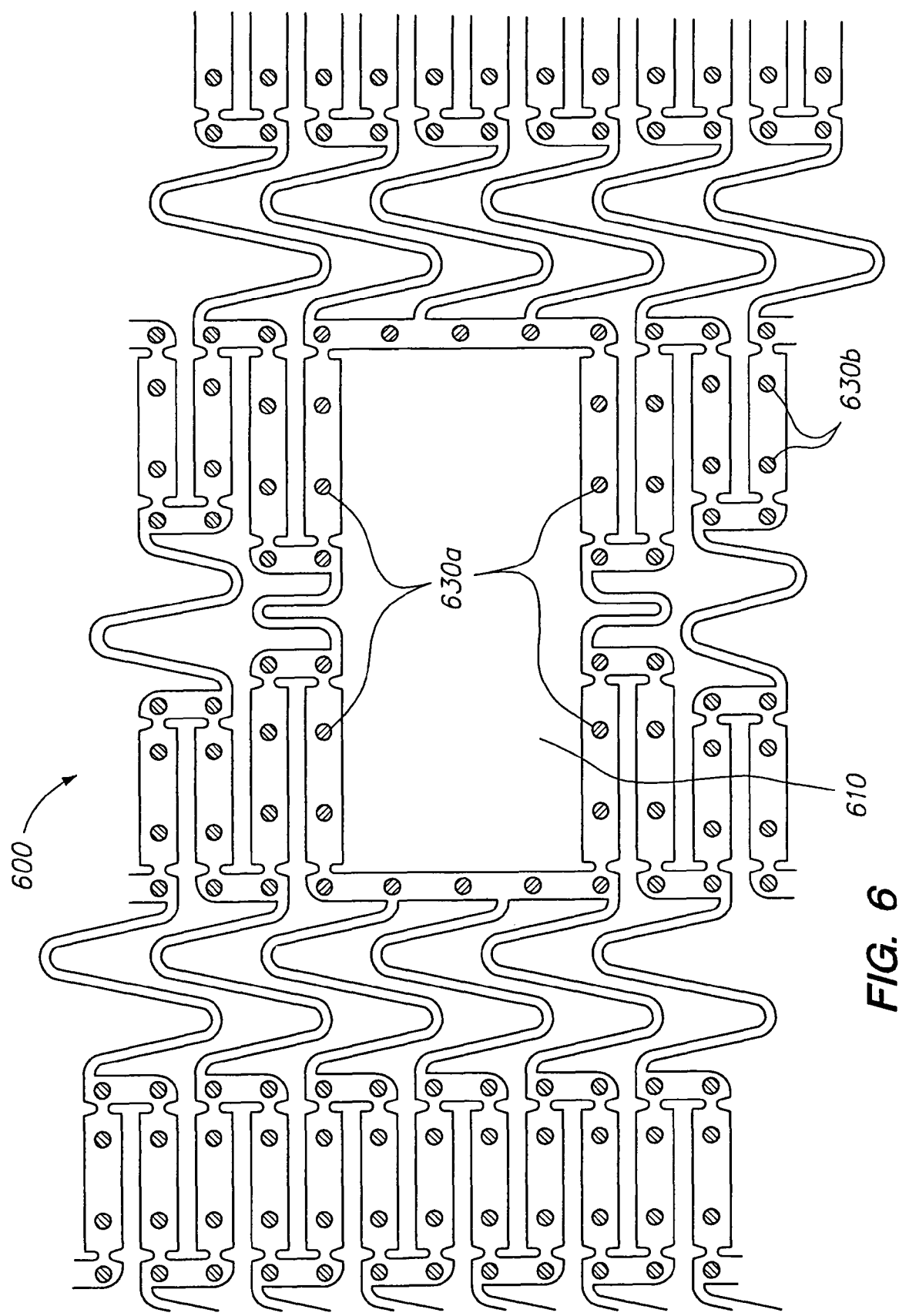
FIG. 6 is an enlarged side view of a portion of an expandable medical device with a bifurcation opening.

Another example of an application for the use of different beneficial agents in different openings is in an expandable medical device 600, as shown in FIG. 6, configured for use at a bifurcation in a vessel. Bifurcation devices include a side hole 610 which is positioned to allow blood flow through a side branch of a vessel. One example of a bifurcation device is described in U.S. Pat. No. 6,293,967 which is incorporated herein by reference in its entirety. The bifurcation device 600 includes the side hole feature 610 interrupting the regular pattern of beams which form a remainder of the device. Since an area around a bifurcation is a particularly problematic area for restenosis, a concentration of an antiproliferative drug may be increased in openings 830a at an area surrounding the side hole 610 of the device 600 to deliver increased concentrations of the drug where needed. The remaining openings 630b in an area away from the side opening contain a beneficial agent with a lower concentration of the antiproliferative. The increased antiproliferative delivered to the region surrounding the bifurcation hole may be provided by a different beneficial agent containing a different drug or a different beneficial agent containing a higher concentration of the same drug.

In addition to the delivery of different beneficial agents to the mural side of the expandable medical device for treatment of the vessel wall, beneficial agents may be delivered to the luminal side of the expandable medical device. Drugs which are delivered into the blood stream from the luminal side of the device can be located at a proximal end of the device or a distal end of the device.

The methods for loading different beneficial agents into different openings in an expandable medical device may include known techniques such as dipping and coating and also known piezoelectric micro-jetting techniques. Micro-injection devices may be computer controlled to deliver precise amounts of two or more liquid beneficial agents to precise locations on the expandable medical device in a known manner. For example, a dual agent jetting device may deliver two agents simultaneously or sequentially into the openings. When the beneficial agents are loaded into through openings in the expandable medical device, a luminal side of the through openings may be blocked during loading by a resilient mandrel allowing the beneficial agents to be delivered in liquid form, such as with a solvent. The beneficial agents may also be loaded by manual injection devices.

Example 1

Figure 7:
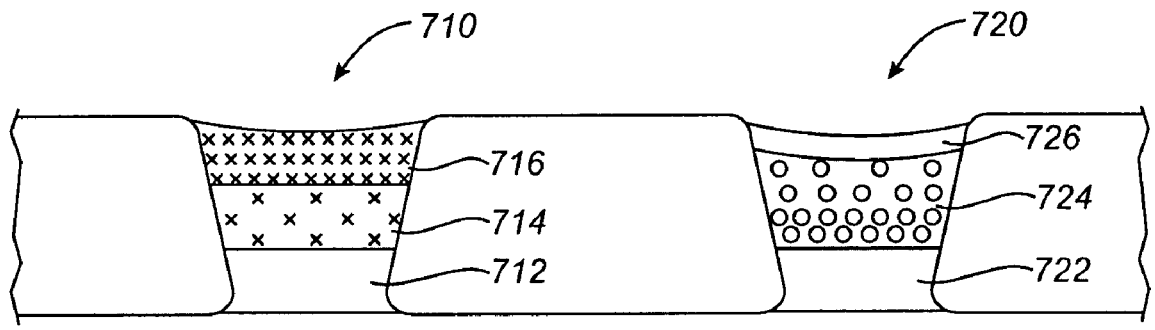
FIG. 7 is a cross sectional view of an expandable medical device having a combination of a first agent, such as an anti-inflammatory agent, in a first plurality of holes and a second agent, such as an anti-proliferative agent, in a second plurality of holes.

FIG. 7 illustrates a dual drug stent 700 having an anti-inflammatory agent and an antiproliferative agent delivered from different holes in the stent to provide independent release kinetics of the two drugs which are specifically programmed to match the biological processes of restenosis. According to this example, the dual drug stent includes the anti-inflammatory agent pimecrolimus in a first set of openings 710 in combination with the antiproliferative agent paclitaxel in a second set of openings 720. Each agent is provided in a matrix material within the holes of the stent in a specific inlay arrangement designed to achieve the release kinetics shown in FIG. 8. Each of the drugs are delivered primarily murally for treatment of restenosis.

As shown in FIG. 7, pimecrolimus is provided in the stent for directional delivery to the mural side of the stent by the use of a barrier 712 at the luminal side of the hole. The barrier 712 is formed by a biodegradable polymer. The pimecrolimus is loaded within the holes in a manner which creates a release kinetic having dual phases. A first phase of the release of pimecrolimus is provided by a murally located region 716 of the matrix which has a fast release formulation including pimecrolimus and biodegradable polymer (PLGA) with a high percentage of drug, such as about 90% drug to 10% polymer. A second phase of the release is provided by a central region 714 of the matrix with pimecrolimus and biodegradable polymer (PLGA) in a ratio of about 50% drug to 50% polymer. As can be seen on the graph of FIG. 8, the first phase of the pimecrolimus release delivers about 50% of the loaded drug in about the first 24 hours. The second phase of the release delivers the remaining 50% over about two weeks. This release is specifically programmed to match the progression of the inflammatory process following angioplasty and stenting. In addition to or as an alternative to changing the drug concentration between the two regions to achieve the two phase release, different polymers or different comonomer ratios of the same polymer can be used in two drug different regions to achieve the two different release rates.

Figure 8:
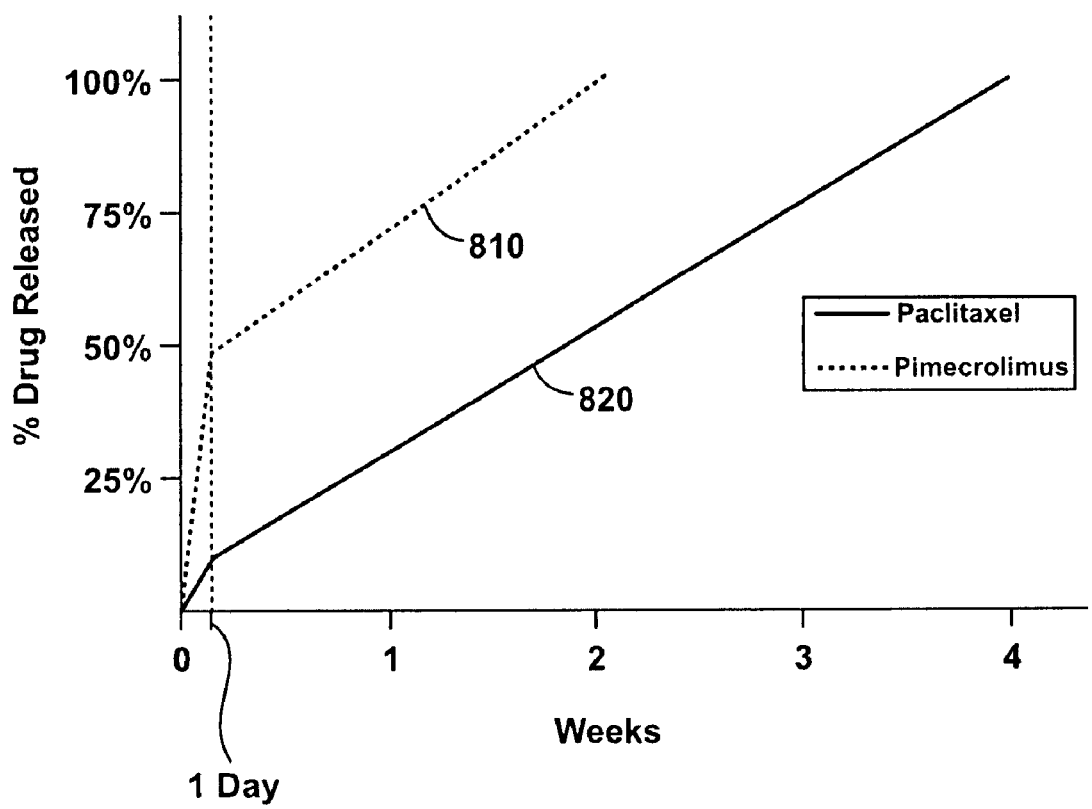
FIG. 8 is a graph of the release rates of one example of an anti-inflammatory and an anti-proliferative delivered by the expandable medical device of FIG. 7.

The paclitaxel is loaded within the openings 720 in a manner which creates a release kinetic having a substantially linear release after the first approximately 24 hours, as shown in FIG. 8. The paclitaxel openings 720 are loaded with three regions including a base region 722 of primarily polymer with minimal drug at a luminal side of the hole, a central region 724 with paclitaxel and polymer (PLGA) provided in a concentration gradient, and a cap region 726 with primarily polymer which controls release of the paclitaxel. The paclitaxel is released with an initial release in the first day of about 5-15% of the total drug load followed by a substantially linear release for about 20-90 days. Additional examples of arrangements for paclitaxel in the holes with a concentration gradient are described in WO 04/110302 described above.

FIG. 7 shows the drug, barrier, and cap regions as distinct regions within the openings for ease of illustration. It should be understood that these regions indistinct and formed by a blending of the different areas. Thus, although the barrier layers are primarily polymer without drug, depending on the manufacturing processes employed, some small amount of drug of the subsequent region can be incorporation into the barrier region.

The amount of the drugs delivered varies depending on the size of the stent. For a 3 mm by 6 mm stent the amount of pimecrolimus is about 50 to about 300 μg, preferably about 100 to about 250 μg. The amount of paclitaxel delivered from this stent is about 5 to about 50 μg, preferably about 10 to about 30 μg. In one example, about 200 μg of pimecrolimus and about 20 μg of paclitaxel are delivered. The drugs may be located in alternating holes in the stent. However, in view of the large difference in the doses to be delivered between the two drugs, it may be desirable to place the paclitaxel in every third of fourth hole in the stent. Alternatively, the holes for delivery of the low dose drug (paclitaxel) can be made smaller than the holes for the high dose.

The polymer/drug inlays are formed by computer controlled piezoelectric injection techniques as described in WO 04/026182 published on Apr. 1, 2004, which is incorporated herein by reference in its entirety. The inlays of the first agent can be formed first followed by the inlays of the second agent using the piezoelectric injector. Alternatively, the system of WO 04/02182 can be equipped with dual piezoelectric dispensers for dispensing the two agents at the same time.

Example 2

According to this example, the dual drug stent includes the Gleevec in the first set of openings 710 in combination with the antiproliferative agent paclitaxel in the second set of openings 720. Each agent is provided in a matrix material within the holes of the stent in a specific inlay arrangement designed to achieve the release kinetics shown in FIG. 8.

The Gleevec is delivered with a two phase release including a high initial release in the first day and then a slow release for 1-2 weeks. The first phase of the Gleevec release delivers about 50% of the loaded drug in about the first 24 hours. The second phase of the release delivers the remaining 50% over about one-two weeks. The paclitaxel is loaded within the openings 720 in a manner which creates a release kinetic having a substantially linear release after the first approximately 24 hours, as shown in FIG. 8 and as described above in Example 1.

The amount of the drugs delivered varies depending on the size of the stent. For a 3 mm by 6 mm stent the amount of Gleevec is about 200 to about 500 μg, preferably about 300 to about 400 μg. The amount of paclitaxel delivered from this stent is about 5 to about 50 μg, preferably about 10 to about 30 μg. As in example 1, the drugs may be located in alternating holes in the stent or interspersed in a non-alternating manner. The polymer/drug inlays are formed in the manner described in Example 1.

Example 3

According to this example, the dual drug stent includes the PKC-412 (a cell growth regulator) in the first set of openings in combination with the antiproliferative agent paclitaxel in the second set of openings. Each agent is provided in a matrix material within the holes of the stent in a specific inlay arrangement designed to achieve the release kinetics discussed below.

The PKC-412 is delivered at a substantially constant release rate after the first approximately 24 hours, with the release over a period of about 4-16 weeks, preferably about 6-12 weeks. The paclitaxel is loaded within the openings in a manner which creates a release kinetic having a substantially linear release after the first approximately 24 hours, with the release over a period of about 4-16 weeks, preferably about 6-12 weeks.

The amount of the drugs delivered varies depending on the size of the stent. For a 3 mm by 6 mm stent the amount of PKC-412 is about 100 to about 400 μg, preferably about 150 to about 250 μg. The amount of paclitaxel delivered from this stent is about 5 to about 50 μg, preferably about 10 to about 30 μg. As in example 1, the drugs may be located in alternating holes in the stent or interspersed in a non-alternating manner. The polymer/drug inlays are formed in the manner described in Example 1.

Therapeutic Agents

The present invention relates to the delivery of anti-restenotic agents including paclitaxel, rapamycin, cladribine (CdA), and their derivatives, as well as other cytotoxic or cytostatic agents and microtubule stabilizing agents. Although anti-restenotic agents have been primarily described herein, the present invention may also be used to deliver other agents alone or in combination with anti-restenotic agents. Some of the therapeutic agents for use with the present invention which may be transmitted primarily luminally, primarily murally, or both and may be delivered alone or in combination include, but are not limited to, antiproliferatives, antithrombins, immunosuppressants including rapamycin, antilipid agents, anti-inflammatory agents, antineoplastics, antiplatelets, angiogenic agents, anti-angiogenic agents, vitamins, antimitotics, metalloproteinase inhibitors, NO donors, estradiols, anti-sclerosing agents, and vasoactive agents, endothelial growth factors, estrogen, beta blockers, AZ blockers, hormones, statins, insulin growth factors, antioxidants, membrane stabilizing agents, calcium antagonists, retenoid, bivalirudin, phenoxodiol, etoposide, ticlopidine, dipyridamole, and trapidil alone or in combinations with any therapeutic agent mentioned herein. Therapeutic agents also include peptides, lipoproteins, polypeptides, polynucleotides encoding polypeptides, lipids, protein-drugs, protein conjugate drugs, enzymes, oligonucleotides and their derivatives, ribozymes, other genetic material, cells, antisense, oligonucleotides, monoclonal antibodies, platelets, prions, viruses, bacteria, and eukaryotic cells such as endothelial cells, stem cells, ACE inhibitors, monocyte/macrophages or vascular smooth muscle cells to name but a few examples. The therapeutic agent may also be a pro-drug, which metabolizes into the desired drug when administered to a host. In addition, therapeutic agents may be pre-formulated as microcapsules, microspheres, microbubbles, liposomes, niosomes, emulsions, dispersions or the like before they are incorporated into the therapeutic layer. Therapeutic agents may also be radioactive isotopes or agents activated by some other form of energy such as light or ultrasonic energy, or by other circulating molecules that can be systemically administered. Therapeutic agents may perform multiple functions including modulating angiogenesis, restenosis, cell proliferation, thrombosis, platelet aggregation, clotting, and vasodilation.

Anti-inflammatories include but are not limited to non-steroidal anti-inflammatories (NSAID), such as aryl acetic acid derivatives, e.g., Diclofenac; aryl propionic acid derivatives, e.g., Naproxen; and salicylic acid derivatives, e.g., Diflunisal. Anti-inflammatories also include glucocoriticoids (steroids) such as dexamethasone, aspirin, prednisolone, and triamcinolone, pirfenidone, meclofenamic acid, tranilast, and nonsteroidal anti-inflammatories. Anti-inflammatories may be used in combination with antiproliferatives to mitigate the reaction of the tissue to the antiproliferative.

The agents can also include anti-lymphocytes; anti-macrophage substances; immunomodulatory agents; cyclooxygenase inhibitors; anti-oxidants; cholesterol-lowering drugs; statins and angiotens in converting enzyme (ACE); fibrinolytics; inhibitors of the intrinsic coagulation cascade; antihyperlipoproteinemics; and anti-platelet agents; anti-metabolites, such as 2-chlorodeoxy adenosine (2-CdA or cladribine); immuno-suppressants including sirolimus, everolimus, tacrolimus, etoposide, and mitoxantrone; anti-leukocytes such as 2-CdA, IL-1 inhibitors, anti-CD116/CD18 monoclonal antibodies, monoclonal antibodies to VCAM or ICAM, zinc protoporphyrin; anti-macrophage substances such as drugs that elevate NO; cell sensitizers to insulin including glitazones; high density lipoproteins (HDL) and derivatives; and synthetic facsimile of HDL, such as lipator, lovestatin, pranastatin, atorvastatin, simvastatin, and statin derivatives; vasodilators, such as adenosine, and dipyridamole; nitric oxide donors; prostaglandins and their derivatives; anti-TNF compounds; hypertension drugs including Beta blockers, ACE inhibitors, and calcium channel blockers; vasoactive substances including vasoactive intestinal polypeptides (VIP); insulin; cell sensitizers to insulin including glitazones, P par agonists, and metformin; protein kinases; antisense oligonucleotides including resten-NG; antiplatelet agents including tirofiban, eptifibatide, and abciximab; cardio protectants including, VIP, pituitary adenylate cyclase-activating peptide (PACAP), apoA-I milano, amlodipine, nicorandil, cilostaxone, and thienopyridine; cyclooxygenase inhibitors including COX-1 and COX-2 inhibitors; and petidose inhibitors which increase glycolitic metabolism including omnipatrilat. Other drugs which may be used to treat inflammation include lipid lowering agents, estrogen and progestin, endothelin receptor agonists and interleukin-6 antagonists, and Adiponectin.

Agents may also be delivered using a gene therapy-based approach in combination with an expandable medical device. Gene therapy refers to the delivery of exogenous genes to a cell or tissue, thereby causing target cells to express the exogenous gene product. Genes are typically delivered by either mechanical or vector-mediated methods.

Some of the agents described herein may be combined with additives which preserve their activity. For example additives including surfactants, antacids, antioxidants, and detergents may be used to minimize denaturation and aggregation of a protein drug. Anionic, cationic, or nonionic detergents may be used. Examples of nonionic additives include but are not limited to sugars including sorbitol, sucrose, trehalose; dextrans including dextran, carboxy methyl (CM) dextran, diethylamino ethyl (DEAE) dextran; sugar derivatives including D-glucosaminic acid, and D-glucose diethyl mercaptal; synthetic polyethers including polyethylene glycol (PEF and PEO) and polyvinyl pyrrolidone (PVP); carboxylic acids including D-lactic acid, glycolic acid, and propionic acid; detergents with affinity for hydrophobic interfaces including n-dodecyl-β-D-maltoside, n-octyl-β-D-glucoside, PEO-fatty acid esters (e.g. stearate (myrj 59) or oleate), PEO-sorbitan-fatty acid esters (e.g. Tween 80, PEO-20 sorbitan monooleate), sorbitan-fatty acid esters (e.g. SPAN 60, sorbitan monostearate), PEO-glyceryl-fatty acid esters; glyceryl fatty acid esters (e.g. glyceryl monostearate), PEO-hydrocarbon-ethers (e.g. PEO-10 oleyl ether; triton X-100; and Lubrol. Examples of ionic detergents include but are not limited to fatty acid salts including calcium stearate, magnesium stearate, and zinc stearate; phospholipids including lecithin and phosphatidyl choline; CM-PEG; cholic acid; sodium dodecyl sulfate (SDS); docusate (AOT); and taumocholic acid.

While the invention has been described in detail with reference to the preferred embodiments thereof, it will be apparent to one skilled in the art that various changes and modifications can be made and equivalents employed, without departing from the present invention.

The invention claimed is:

1. An expandable medical device for delivery of a beneficial agent, the device comprising:
   a substantially cylindrical device which is expandable from a cylinder having a first diameter to a cylinder having a second diameter;
   a first plurality of openings formed in the substantially cylindrical device containing a first beneficial agent for delivery to tissue, wherein the first beneficial agent is arranged to be delivered according to a first release curve to target a restenosis; and
   a second plurality of openings formed in the substantially cylindrical device containing a second beneficial agent for delivery to tissue, wherein the second beneficial agent is arranged to be delivered according to a second release curve different from the first release curve to target a disease other than restenosis; and wherein the first beneficial agent is delivered with at least 40% of the drug delivered in the first 24 hours and the second beneficial agent delivered with less than 20% of the drug delivered in the first 24 hours.

2. The expandable medical device according to claim 1, wherein the first beneficial agent is insulin.

* * * * *